United States Patent [19]

Kurihara et al.

[11] Patent Number: 5,494,605
[45] Date of Patent: Feb. 27, 1996

[54] P-TERPHENYL DERIVATIVES AND LIQUID CRYSTALLINE COMPOSITIONS

[75] Inventors: Makoto Kurihara; Hiromi Inoue; Atsushi Sugiura; Kenji Suzuki; Tsunenori Fujii, all of Soka, Japan

[73] Assignee: Kanto Kagaku Kabushiki Kaisha, Tokyo, Japan

[21] Appl. No.: 157,339

[22] Filed: Nov. 24, 1993

Related U.S. Application Data

[63] Continuation of Ser. No. 980,431, Nov. 23, 1992, abandoned, which is a continuation of Ser. No. 397,964, Aug. 24, 1989, abandoned.

[30] Foreign Application Priority Data

Sep. 1, 1988 [JP] Japan .................. 63-216294

[51] Int. Cl.$^6$ .................................. C09K 19/12
[52] U.S. Cl. .................. 252/299.66; 560/59; 560/65; 560/141; 568/642; 568/661; 570/129
[58] Field of Search .................. 252/299.01, 299.6, 252/299.66; 568/631, 633, 642, 661; 560/59, 65, 141; 570/129

[56] References Cited

U.S. PATENT DOCUMENTS

| | | | |
|---|---|---|---|
| 4,594,465 | 6/1986 | Kam Ming Chan | 252/299.66 |
| 4,696,549 | 9/1987 | Kam Ming Chan | 252/299.66 |
| 4,780,240 | 10/1988 | Emoto et al. | 252/299.66 |
| 4,808,333 | 2/1989 | Huynh-ba | 252/299.66 |
| 4,943,387 | 7/1990 | Furukawa et al. | 252/299.66 |
| 5,064,569 | 11/1991 | Geelhaar et al. | 252/299.66 |
| 5,273,680 | 12/1993 | Gray et al. | 252/299.66 |

FOREIGN PATENT DOCUMENTS

| | | |
|---|---|---|
| 0084194 | 7/1983 | European Pat. Off. . |
| 0132377 | 1/1985 | European Pat. Off. . |
| 0278665 | 8/1988 | European Pat. Off. . |
| 2200912 | 8/1988 | United Kingdom . |
| 8802130 | 3/1988 | WIPO . |
| 8912039 | 12/1989 | WIPO . |
| 9002161 | 3/1990 | WIPO . |

OTHER PUBLICATIONS

"Ferroelectric Liquid Crystals", R. B. Meyer et al, Le Journal De Physique—Lettres No. 0009, Jan. 9, 1975.

"Submicrosecond bistable electro-optic switching in liquid crystals", N. Clark et al, Applied Physics Letter, American Institute of Physics, Mar. 13, 1980.

"Synthesis and Evaluation of Some 4,4"-Disubstituted Lateral Fluoro-1,1': 4',1"-terphenyls", L. K. M. Chan et al, Mol. Cryst. Liq. Cryst. 1985 vol. 123, pp. 185–204.

Primary Examiner—Philip Tucker
Attorney, Agent, or Firm—Birch, Stewart, Kolasch & Birch

[57] ABSTRACT

The p-terphenyl derivatives of the formula shown below are useful in preparing practical ferroelectric liquid crystalline compositions. The derivatives exhibit excellent chemical stability and display the chiral smectic C or smectic C phase over a wide temperature range.

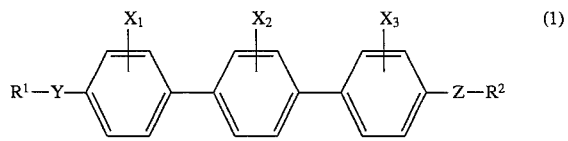

wherein each of $R_1$ and $R_2$ is a straight or branched chain alkyl group having 1–18 carbon atoms; each of Y and Z is a single bond, O, COO or OCO; and any two of $X_1$, $X_2$, and $X_3$ are fluorine atoms and the remainder is a hydrogen atom.

4 Claims, No Drawings

P-TERPHENYL DERIVATIVES AND LIQUID CRYSTALLINE COMPOSITIONS

This application is a continuation of application Ser. No. 07/980,431 filed on Nov. 23, 1992, now abandoned, which is a continuation under 37 CFR 1.62 of prior application Ser. No. 07/397,964, filed on Aug. 24, 1989, now abandoned.

BACKGROUND OF THE INVENTION

1. Field of the Invention

The present invention relates to new liquid crystalline compounds as well as liquid crystalline compositions containing at least one of the liquid crystalline compounds. More particularly, the present invention relates to ferroelectric liquid crystals and to new p-terphenyl derivatives which are useful as components for preparing practical ferroelectric liquid crystalline compositions and excellent in chemical stability as well as liquid crystalline compositions containing at least one of the p-terphenyl derivatives.

2. Description of the Prior Art

Liquid crystal display elements are widely used as display elements in watches, electronic desk-top computers, personal word processors, pocket-size TV sets, etc. They possess such beneficial characteristics as no eyestrain, because of their passive device, low electric power consumption, thin structure, etc. However, they are restricted in their practical applications because of slow response time and lack of memory effect. In an attempt to expand their areas of application there have been provided, for example, the super twisted nematic (STN) display system, which is an improvement of the twisted nematic (TN) display system. These systems, however, are not sufficient for large screen or graphic display use. Various studies have therefore been made of liquid crystal display elements which can supersede them. One such display system [N. A. Clark et al., Applied Phys. lett., 36, 899 (1980)] utilizes ferroelectric liquid crystals [R. B. Meyer et al., Physique, 36 L-69 (1975)]. Because of its advantageous characteristics such as fast response, which is 100 times conventional systems, and memory effect, it is expected to expand areas of application of liquid crystal display elements. The term "ferroelectric liquid crystal" is used to mean a series of smectic liquid crystals whose molecular longitudinal axis is at a certain angle to the normal of the layer, but in practice the chiral smectic C (SmC*) phase is utilized.

In practice, ferroelectric liquid crystals for display elements are used as a liquid crystalline composition comprising a number of ferroelectric liquid crystalline compounds or prepared by blending such compound(s) and one or more compounds having the smectic C (SmC) phase. As is the case with the preparation of nematic liquid crystal display elements, mixing a number of components is required if different properties needed for actual use, such as operating temperature range, response time, helical pitch, chemical stability and so on, are to be achieved.

Ferroelectric liquid crystalline compositions have not been put to actual use as of yet. In particular, there has been a need for the development of substances which show the SmC phase over a wide temperature range, and which have the SmC* phase and an adequate spontaneous polarization value. The object of the present invention is to provide new substances which satisfy such a need.

Known p-terphenyl compounds of analogous structure are disclosed, for example, in EP-013277, GB-2200912 and Mol. Cryst. Liq. Cryst., 1985, Vol. 123, pp. 185–204.

The present invention provides substances which have a wider temperature range for the SmC or SmC* phase than these known compounds, as well as substances which have SmC* phase and an adequate spontaneous polarization value.

SUMMARY OF THE INVENTION

The present inventors designed, synthesized, evaluated and extensively studied compounds of different new structures, paying particular attention to their temperature range in which a ferroelectric property is shown. As a result the inventors have succeeded in providing new p-terphenyl derivatives which have a wide temperature range for the SmC* or SmC phase as well as chemical stability and excellent response time.

DETAILED DESCRIPTION OF THE INVENTION

The present invention thus provides p-terphenyl derivatives of the general formula

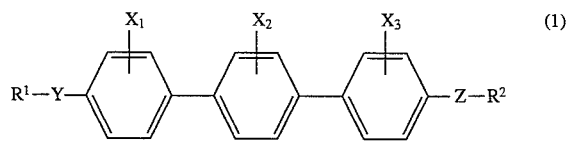

(1)

wherein each of $R^1$ and $R^2$ is a straight or branched chain alkyl group having 1–18 carbon atoms; each of Y and Z is a single bond, O, COO or OCO; and any two of $X_1$, $X_2$ and $X_3$ are fluorine atoms and the remainder is a hydrogen atom, as well as liquid crystalline compositions containing at least one of these derivatives.

The new compounds according to the present invention, even when used individually, exhibit the SmC or SmC* phase over a wide temperature range. Ferroelectric liquid crystalline compositions with an even wider temperature range for the SmC* phase, are obtainable by preparing mixtures of these compounds or mixtures of one or more such compounds with one or more other liquid crystalline compounds or compositions.

Accordingly, the p-terphenyl derivatives according to the present invention are useful as components for preparing ferroelectric liquid crystalline compositions for use in ferroelectric liquid crystal display elements.

Processes for their preparation will be described below in detail by showing synthetic routes, working examples etc. The phase transition temperature of synthesized compounds will be affected by the measuring instrument or method and the purity of the substance. Thus, it is to be understood that measured values will vary.

The new p-terphenyl derivatives according to the present invention can be synthesized through a variety of routes, for example according to the routes schematized below.

Schematized synthetic route example I
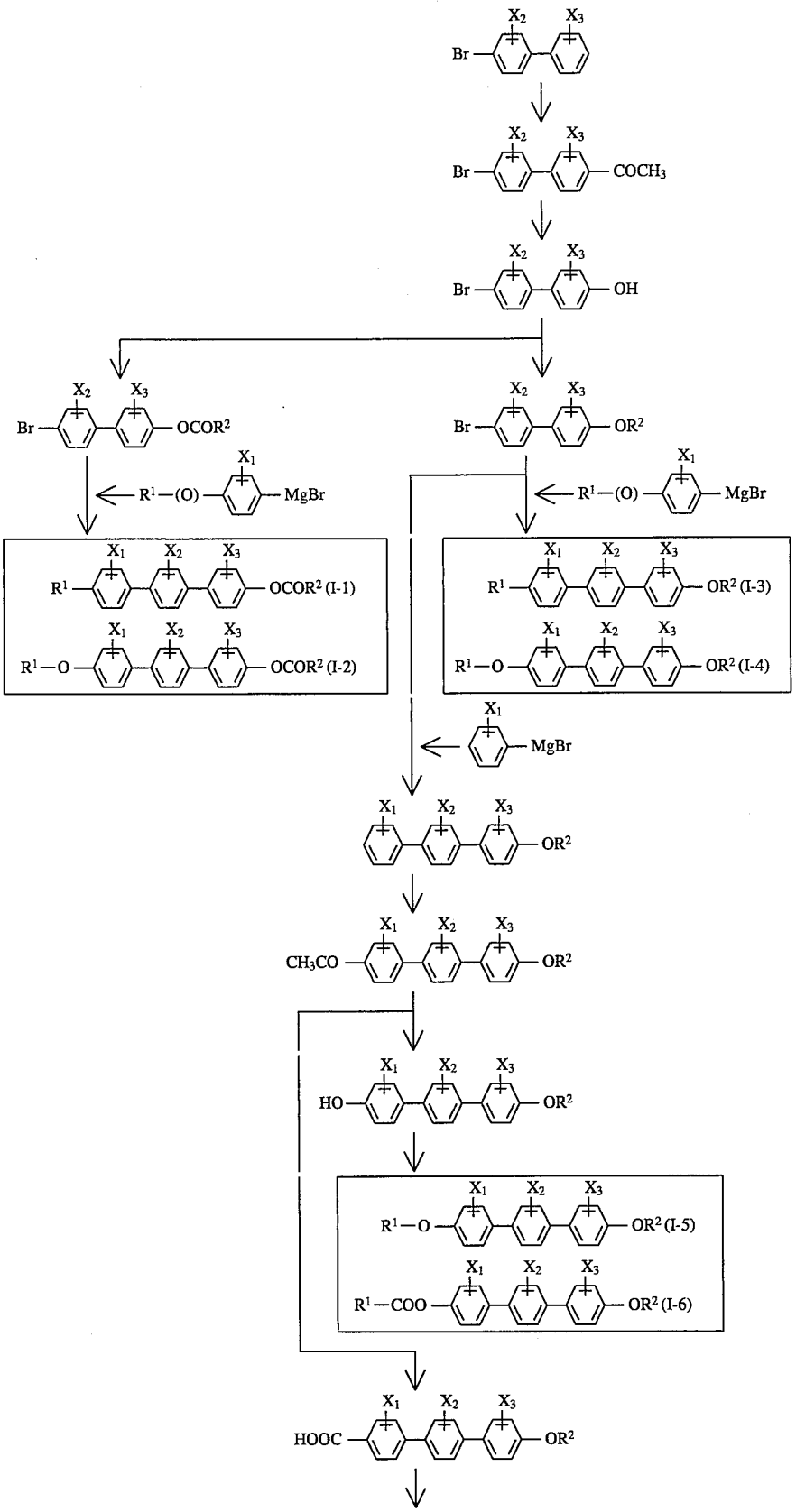

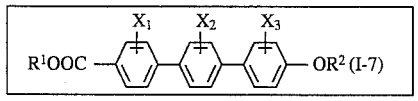
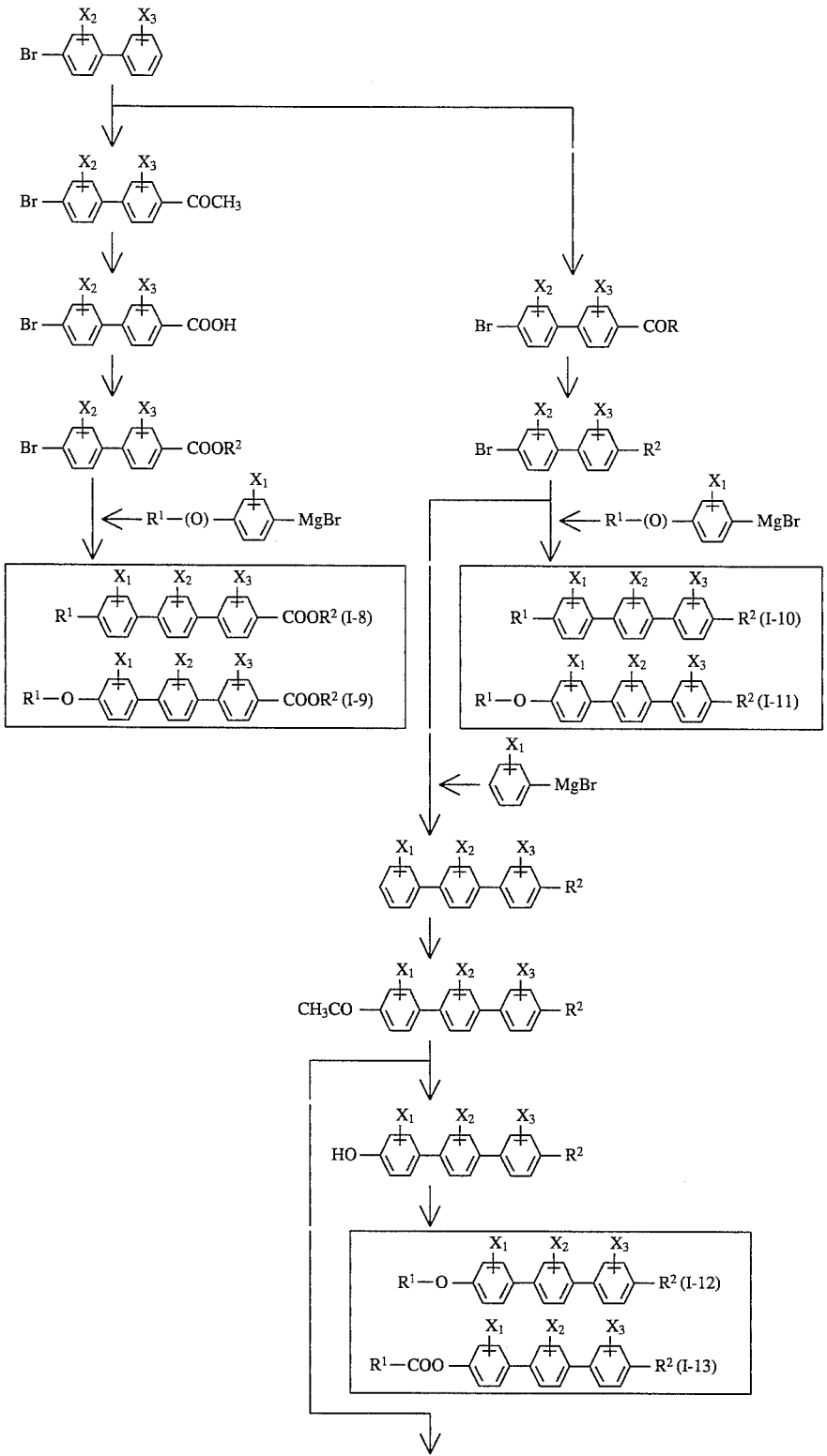

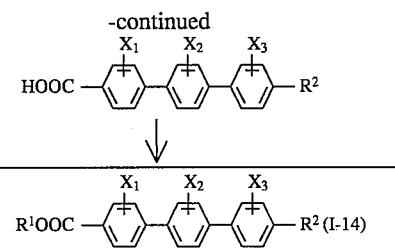

Schematized synthetic route example II

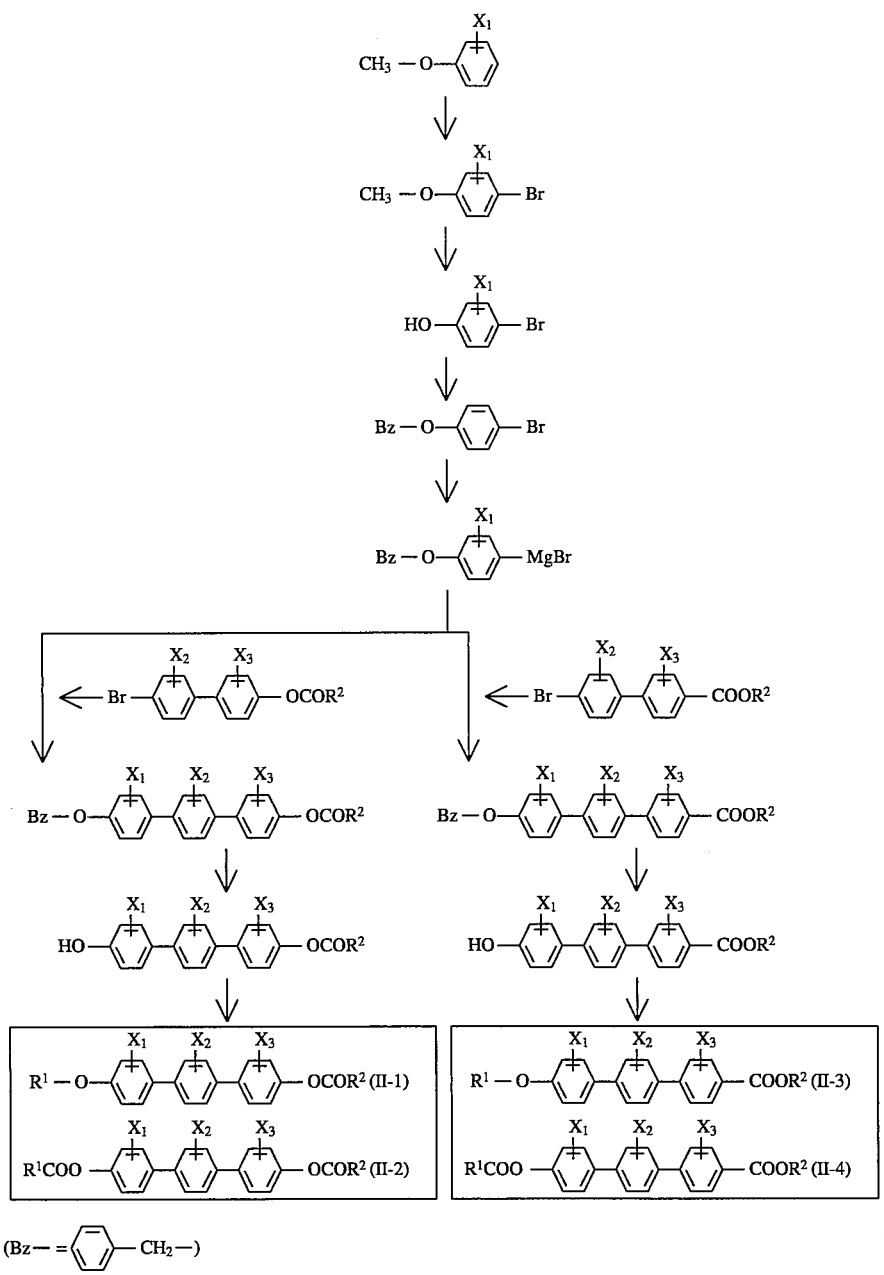

The schematized synthetic routes will now be described below.

4-Alkyloxy-4"-alkyloxy-p-terphenyls and derivatives thereof (I-4) can be synthesized by subjecting 4-bromobiphenyl or its derivative as starting material to acetylation, Baeyer-Villiger oxidation, hydrolysis and etherification and then to cross-coupling reaction with a Grignard reagent prepared from a 4-alkyloxybromobenzene or its derivative. 4-Alkyloxycarbonyl- 4"-alkyl-p-terphenyls and derivatives thereof (I-14) can be synthesized by subjecting 4-bromobiphenyl or its derivative as starting material to acylation, reduction, cross-coupling reaction with a Grignard reagent prepared from bromobenzene or its derivative, acetylation, haloform oxidation and esterification. 4-acyloxy-4"-alkyloxycarbonyl-p-terphenyls and derivatives thereof (II-4) can be synthesized by subjecting anisole or its derivative as starting material to bromination, ether-cleavage and benzyletherification followed by conversion into a Grignard reagent, which is then subjected to cross-coupling reaction with a 4-bromo-4'-alkyloxycarbonyl-biphenyl or its derivative followed by ether-cleavage and esterification. The other end compounds (I-1, I- 2, I-3, I-5, I-6, I-7, I-8, I-9, I-10, I-11, I-12, I-13, II-1, II-2 and II-3) shown in "Schematized synthetic route examples" can be synthesized by appropriately combining the above mentioned reactions in respective processes.

In the examples given below, the notations and abbreviations are used to mean the following:
 GLC : gass chromatography
 HPLC high ; performance liquid chromatography
 IR : infra-red rays absorption spectroscopy
 Mass : mass spectrometry
 m.p. : melting point
 C : crystals
 Sx : unidentified smectic phase
 SB : smectic B phase
 SmC, Sc : smectic C phase
 SmC*, Sc* : chiral smectic C phase
 SA : smectic A phase
 Ch : cholesteric phase
 I : isotropic liquid
 ? : temperature being indefinite Example 1

(a) Synthesis of

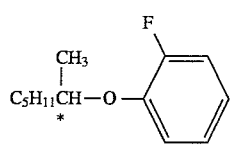

A reaction vessel was charged with 10 g of 2-fluorophenol, 25 g of (S)-1-methylhexyl tosylate, 20 g of potassium carbonate and 160 ml of MEK, and the mixture was refluxed with stirring for 14 hours (the disappearance of the starting materials was confirmed by TLC). The reaction liquid was poured into diluted hydrochloric acid and the mixture was extracted with benzene. The extract was washed with water and dried over Glauber's salt, and the solvents were distilled off. The residue was distilled under reduced pressure to obtain 14 g (74.5%) of (R) -2- (1-methylhexyl) oxyfluorobenzene.
 b.p. 113°–117° C./9 mmHg
(b) Synthesis of

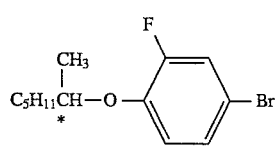

A reaction vessel was charged with 13.9 g of (R)-2-(1-methylhexyl)oxyfluorobenzene obtained in (a) above and 50 ml of chloroform. To the mixture was added dropwise 12.7 g of bromine with stirring at room temperature. The resultant mixture was further stirred at room temperature (until the starting materials were confirmed by GLC to have disappeared) and a 10% aqueous solution of caustic soda was added with stirring. The organic layer was washed with water and dried over Glauber's salt. The solvents were distilled off and the residue was distilled under reduced pressure to obtain 14.2 g (74.1%) of (R)-4-(1-methylhexyl)oxy-3-fluorobromobenzene.
 b.p. 98°–110° C./0.3 mmHg
(c) Synthesis of

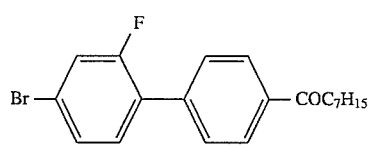

A reaction vessel was charged with 20 ml of methylene chloride and 3.2 g of anhydrous aluminum chloride. To the mixture was added 4 g of octanoyl chloride with stirring at a temperature not higher than −5° C. and was then added dropwise a solution of 3 g of 4-bromo-2-fluorobiphenyl in 10 ml of methylene chloride.

After the dropwise addition, the mixture was reacted for 3 hours with stirring at a temperature not higher than 0° C. and then allowed to stand overnight at room temperature. The reaction liquid was poured into ice/diluted hydrochloric acid and the mixture was extracted with benzene. The benzene solution was washed with water, treated with diluted aqueous ammonia, washed with water and then dried over Glauber's salt. The benzene was distilled off and the residue was recrystallized from acetone to obtain 3.8 g (84.2%) of 4-octanoyl- 2'-fluoro-4'-bromobiphenyl.
 TLC monospot
(b) Synthesis of

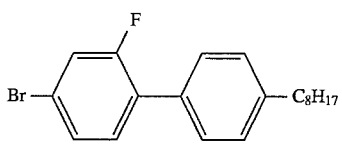

A reaction vessel was charged with 3.75 g of 4-octanoyl-2'-fluoro-4'-bromobiphenyl obtained in (c) above and 20 ml of trifluoroacetic acid. To the mixture was added dropwise 2.4 g of triethylsilane with stirring at room temperature. After stirring for 6 hours, the reaction liquid was poured into water and the mixture was extracted with benzene. The benzene extract was washed successively with water, an aqueous solution of sodium hydrogen carbonate and water, and then dried over Glauber's salt. The solvents were distilled off and the residue was distilled in a glass tube oven (GTO) to obtain 2.56 g (71.1%) of 4-octyl-2'-fluoro-4'-bromobiphenyl. GTO-set temperature: 150° C./0.2 mmHg.
 TLC monospot
(e) Synthesis of

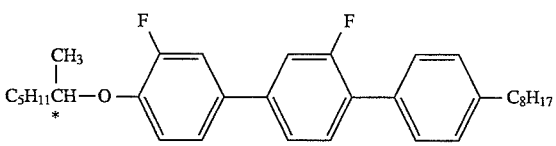

A reaction vessel was charged with 0.4 g of magnesium powder and a small piece of iodine. A small portion of a solution of 3.4 g of (R)-4-(1-methylhexyl) oxy-3-fluorobromobenzene obtained in (b) above in 20 ml of THF was added. After initiation of the reaction (with heating applied where necessary), the remainder of the THF solution was added dropwise with stirring in such a manner that the resultant mixture was kept refluxed. The mixture was refluxed with stirring for a further period of 2 hours to prepare a Grignard reagent.

Another reaction vessel was charged, under a stream of nitrogen, successively with 0.1 g of dichlorobistriphenylphosphinepalladium[ $Cl_2Pd(PPh_3)_2$], 20 ml of dried THF, 0.5 ml of a 1M solution of diisobutylaluminum hydride[(iso-$C_4H_9)_2AlH$] in hexane and a solution of 2.2 g of 4-octyl-2'-fluoro-4'-bromobiphenyl obtained in (d) above in 20 ml of THF. The previously prepared Grignard reagent was added dropwise with stirring at 50° C. and after the dropwise addition the mixture was reacted with stirring for 6 hours at the same temperature. The reaction liquid was poured into diluted hydrochloric acid and the mixture was extracted with benzene. The extract was washed with an aqueous solution of edible salt and dried over Glauber's salt. The solvents were distilled off and the residue was purified by way of column chromatography on silica gel (eluent: hexane/benzene=6:1) and then recrystallized from acetone to obtain 1.3 g (43.6%) of (R)-4-(1-methylhexyl) oxy- 3,3'-difluoro-4"-octyl-p-terphenyl.

The purity of this product was at least 99% by HPLC. The resultant substance was confirmed to be the end product in view of its measurement by IR and its molecular ion peak found at 492 by Mass and in view of the starting materials used.

This product was inserted into a Mettler hot stage FP-82 and its phase transition was observed under a polarization microscope. A result of the observation is shown in Table 1.

Example 2

(a) Synthesis of

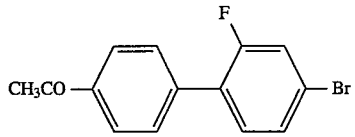

A reaction vessel was charged with 113 g of anhydrous aluminum chloride and 600 ml of methylene chloride. To the mixture was added dropwise 113 g of acetyl chloride with stirring at a temperature not higher than 0° C., and was then added dropwise a solution of 100 g of 4-bromo-2-fluorobiphenyl in 400 ml of methylene chloride. The mixture was reacted with stirring for 7 hours while gradually bringing it back to room temperature. The reaction liquid was poured into ice and diluted hydrochloric acid. The methylene chloride layer was washed successively with water, an aqueous solution of sodium hydrogen carbonate and water, and then dried over Glauber's salt. The solvent was then distilled off and the residue was recrystallized from acetone to give 96 g (82.2%) of 4-acetyl- 2'-fluoro-4'-bromobiphenyl.

GLC 100%

(b) Synthesis of

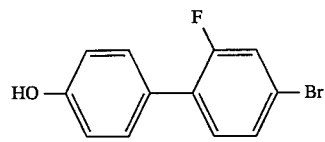

A reaction vessel was charged with 65 g of 4-acetyl-2'-fluoro- 4'-bromobiphenyl obtained in (a) above and 300 ml of methylene chloride. To the mixture was added dropwise 500 ml of 88% formic acid and 480 ml of acetic anhydride with stirring at 10° C. and was then added 1.5 ml of concentrated sulfuric acid. To the resultant mixture was added dropwise 150 ml of 35% aqueous hydrogen peroxide over a period of 3 hours. After the dropwise addition, the mixture was gradually warmed up to 45°–50° C. at which temperature it was reacted with stirring for 30 hours. The reaction liquid was poured into ice water and the mixture was extracted with benzene. The extract was washed with an aqueous solution of sodium hydrogen carbonate and then with water, and dried over Glauber's salt. The solvents were distilled off and the residue obtained and 2 l of ethyl alcohol were charged into another reaction vessel. To the mixture was added a 25% aqueous solution caustic potash and the resultant mixture was refluxed with stirring for 8 hours. The reaction liquid was poured into ice and diluted hydrochloric acid and the mixture was extracted with benzene. The extract was washed with an aqueous solution of edible salt and dried over Glauber's salt. The solvent was distilled off and the residue was purified by way of column chromatography on silica gel using benzene as eluent to obtain 28.1 g (47.5%) of 4-hydroxy-2 '-fluoro-4 '-bromobiphenyl.

(c) Synthesis of

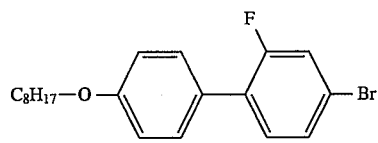

A reaction vessel was charged with 5 g of 4-hydroxy-2'-fluoro- 4'-bromobiphenyl obtained in (b) above, 5.2 g of octyl bromide, 4 g of potassium carbonate and 50 ml of 2-butanone (MEK), and the reaction was effected for 8 hours under reflux with stirring. The reaction liquid was poured into diluted hydrochloric acid and the mixture was extracted with benzene. The extract was washed with water and dried over Glauber's salt and then the solvents were distilled off. The residue was distilled in a glass tube oven (GTO) to obtain a fraction (GTO-set temperature: 150° C./0.2 mmHg), which was then purified by way of column chromatography on silica gel (eluent: hexane) to obtain 6.3 g (88.7%) of 4-octyloxy-2'-fluoro-4'-bromobiphenyl.

(d) Synthesis of

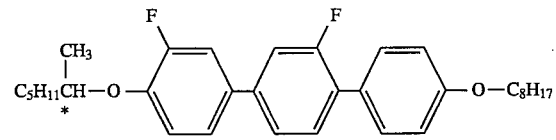

Except that 2.3 g of 4-octyloxy-2'-fluoro-4'-bromobiphenyl obtained in (c) above was used in place of 2.2 g of 4-octyl-2' -fluoro-4'-bromobiphenyl used in Example 1 (e), the same operation was performed in the same manner as in Example 1 (e) to obtain 0.5 g (17%) of (R)-4-(t-methylhexyl)oxy-3,3'-difluoro- 4"-octyloxy-p-terphenyl.

The purity of this product was at least 99% by HPLC. The resultant substance was confirmed to be the end product in view of its measurement by IR and its molecular ion peak found at 508 by Mass and in view of the starting materials used.

This product was inserted into a Mettler hot stage FP-82 and its phase transition was observed under a polarization microscope. A result of the observation is shown in Table 1.

Example 3

(a) Synthesis of

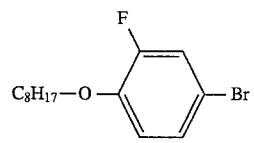

A reaction vessel was charged with 15 g of 2-fluorophenol, 25.9 g of octylbromide, 46.2 g of potassium carbonate and 150 ml of cyclohexanone, and the mixture was stirred at 120°–130° C. for 12 hours. The reaction liquid was poured into diluted hydrochloric acid and the mixture was extracted with benzene. The extract was washed with water and dried over Glauber's salt. The solvents were distilled off, and the residue and 100 ml of chloroform were charged into a separate reaction vessel. With stirring at room temperature 44 g of bromine was added dropwise and the mixture was stirred at the same temperature for 6 hours and then poured into a diluted aqueous solution of caustic soda with stirring. The chloroform layer was washed with water and dried over Glauber's salt. The solvent was distilled off and the residue was distilled under reduced pressure to obtain 32 g (78.8%) of 4-octyloxy-3-fluorobromobenzene.

b.p. 122°–130° C./0.3 mmHg (b) Synthesis of

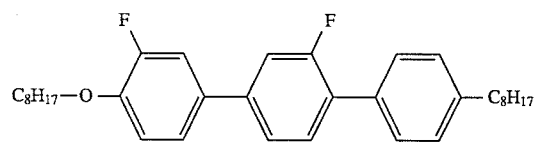

Except that 3.6 g of 4-octyloxy-3-fluorobromobenzene obtained in (a) above was used in place of 3.4 g of (R)-4-(1-methylhexyl)oxy-3-fluorobromobenzene used in Example 1 (e), the operation was performed in the same manner as in Example 1 (e) to obtain 1.0 g (32.6%) of 4-octyloxy-4"-octyl- 3,3'-difluoro-p-terphenyl.

The purity of this product was at least 99% by HPLC. The resultant substance was confirmed to be the end product in view of its measurement by IR and its molecular ion peak found at 506 by Mass and in view of the starting materials used.

This product was inserted into a Mettler hot stage FP-82 and its phase transition was observed under a polarization microscope. A result of the observation is shown in Table 2.

Example 4

Synthesis of

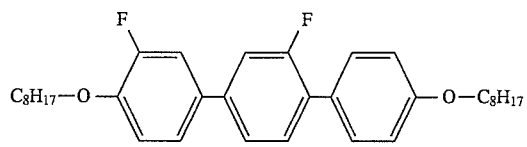

Except that 3.6 g of 4-octyloxy-3-fluorobromobenzene obtained in Example 3 (a) and 2.2 g of 4-octyloxy-2'-fluoro-4'-bromobiphenyl obtained in Example 2 (c) were used in place of 3.4 g of (R) -4-(1-methylhexyl)oxy-3-fluorobromobenzene and 2.2 g of 4-octyl-2'-fluoro-4'-bromobiphenyl used in Example 1 (e), respectively, the operation was performed in the same manner as in Example 1 (e) to obtain 0.42 g (13.9%) of 4,4"-dioctyloxy- 3,3' -difluoro-p-terphenyl.

The purity of this product was at least 98% by HPLC. The resultant substance was confirmed to be the end product in view of its measurement by IR and its molecular ion peak found at 522 by Mass and in view of the starting materials used.

This product was inserted into a Mettler hot stage FP-82 and its phase transition was observed under a polarization microscope. A result of the observation is shown in Table 2.

Example 5

(a) Synthesis of

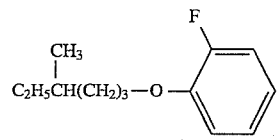

Except that 17 g of racemic-4-methylhexyl bromide was used in place of 25 g of (S)-1- methylhexyl tosylate used in Example 1 (a) , the operation was performed in the same manner as in Example 1 (a) to obtain 15 g (80%) of racemic-2-(4-methylhexyl)oxyfluorobenzene.

b.p. 120°–122° C./7 mmHg (b) Synthesis of

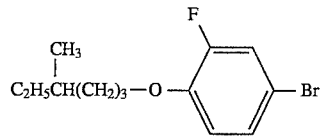

Except that 13.9 g of racemic-2-(4-methylhexyl) oxyfluorobenzene obtained in (a) above was used in place of 13.9 g of (R)-2-(1-methylhexyl)oxyfluorobenzene used in Example 1 (b), the operation was performed in the same manner as in Example 1 (b) to obtain 16.7 g (87%) of racemic-4-(4-methylhexyl)oxy-3-fluorobromobenzene.

b.p. 124°–134° C./0.25 mmHg (c) Synthesis of

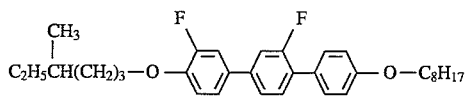

Except that 3.4 g of racemic-4-(4-methylhexyl)oxy-3-fluorobromobenzene obtained in (b) above and 2.2 g of 4-octyloxy- 2'-fluoro-4'-bromobiphenyl obtained in Example 2 (c) were used in place of 3.4 g of (R)-4-(1-methylhexyl)oxy-3-fluorobromobenzene and 2.2 g of 4-octyl-2'-fluoro-4'-bromobiphenyl used in Example 1 (e), respectively, the operation was performed in the same manner as in Example 1 (e) to obtain 0.23 g of racemic-4-(4-methylhexyl) oxy-3,3 '-difluoro 4"-octyloxy-p-terphenyl.

The purity of this product was at least 99% by HPLC. The resultant substance was confirmed to be the end product in view of its measurement by IR and its molecular ion peak found at 508 by Mass and in view of the starting materials used.

This product was inserted into a Mettler hot stage FP-82 and its phase transition was observed under a polarization microscope. A result of the observation is shown in Table 2.

TABLE 1

| Example No. | Phase transition temperature (°C.) | | | | | | | |
|---|---|---|---|---|---|---|---|---|
| | C | $Sx_1$ | $Sx_2$ | $S_B$ | $S_C*$ | $S_A$ | Ch | I |
| 1 | ·47 | | | | (·37.5) | (·40.5) | | · |
| 2 | ·42.5 | | | | ·79.5 | | ·86 | · |

TABLE 2

| Example No. | Phase transition temperature (°C.) | | | | | | |
|---|---|---|---|---|---|---|---|
| | C | $Sx_1$ | $Sx_2$ | $S_B$ | $S_C$ | $S_A$ | I |
| 3 | ·59.5 | | | | ·108.5 | ·127.5 | · |
| 4 | ·80 | ·83 | | | ·149 | ·155.5 | · |
| 5 | ·42.5 | ·52.2 | | | ·139.5 | ·140 | · |

Example 6

A 3 μm-thick liquid crystalline cell, provided with transparent electrodes, was prepared by subjecting the polyvinyl alcohol (PVA) - coated surface to a parallel aligning treatment by rubbing. The compound obtained in Example 2 was enclosed in the liquid crystalline cell and gradually cooled from the isotopic liquid phase to SmC* phase to prepare a liquid crystal element. This liquid crystal element was interposed between two polarization panels and a 200 Hz square wave of±25 V was applied thereto. Response times were determined from changes in intensity of transmission light. As a result, the response time was 180 μsec at 77° C. and 180 μsec also at 50° C., showing a good dependency on temperature.

Example 7

The compound from Example 3, a non-chiral substance with a SmC phase, and that from Example 2, a chiral substance, were mixed together in a ratio of 90:10 by weight to prepare a liquid crystalline composition. This composition showed the SmC* at 56°–104° C. When the composition was used in the same manner as in Example 6 to prepare a liquid crystal element, its response time was found to be 280 μsec (measurement temperature: 102° C.) and 320 μsec (measurement temperature: 70° C.).

Example 8

Each of the compounds obtained in Examples 1 and 2 was mixed, in a ratio of 10:90 by weight, with the following pyrimidine-type liquid crystalline composition, respectively, to prepare new liquid crystalline compositions. These compositions were each used in the same manner as in Example 6 to prepare liquid crystal elements and their response times were determined. The results are shown below.

Pyrimidine-type liquid crystalline composition used:

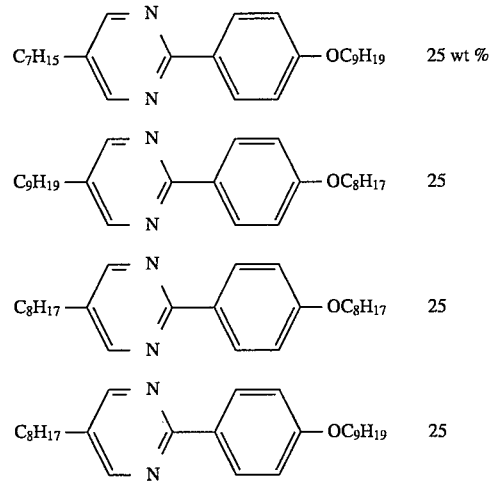

The temperature range for the SmC phase, found upon cooling, of this liquid crystalline composition was 54°-12° C.

| Compound of the invention added | Response time (μ sec) | Measurement temperature (°C.) | SmC* temperature range upon cooling (°C.) |
|---|---|---|---|
| Example 1 | 252 | 49 | 52–2 |
| Example 2 | 241 | 51 | 54–1 |

As is apparent from the above, the compounds of the present invention are useful substances utilizable for the manufacture of practical, ferroelectric liquid crystal display elements. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A p-terphenyl derivative wherein said derivative is represented by the formula:

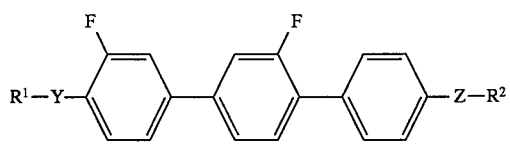

wherein $R^1$ is a straight or branched chain alkyl group having 4–18 carbon atoms and $R^2$ is a straight or branched chain alkyl group having 3–18 carbon atoms; each of Y and Z is selected from the group consisting of a single bond, O, COO and OCO; wherein said derivative exhibits a chiral smectic C phase or a smectic C phase over at least about a 10° C. temperature range.

2. The p-terphenyl derivative according to claim 1, wherein Y is 0 and Z is a single bond or 0.

3. A ferroelectric liquid crystalline composition comprising a p-terphenyl derivative according to claim 1, wherein said composition is capable of exhibiting a ferroelectric response.

4. A ferroelectric liquid crystalline composition comprising a p-terphenyl derivative according to claim 2, wherein said composition is capable of exhibiting a ferroelectric response.

* * * * *